United States Patent
Tass et al.

(10) Patent No.: US 10,350,410 B2
(45) Date of Patent: Jul. 16, 2019

(54) DEVICE AND METHOD FOR EFFECTIVE NON-INVASIVE NEUROSTIMULATION BY MEANS OF VARYING STIMULUS SEQUENCES

(71) Applicant: Forschungszentrum Juelich GmbH, Juelich (DE)

(72) Inventors: Peter Alexander Tass, Juelich (DE); Magteld Zeitler, Malden (NL)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 15/528,157

(22) PCT Filed: Nov. 26, 2015

(86) PCT No.: PCT/EP2015/077802
§ 371 (c)(1),
(2) Date: May 19, 2017

(87) PCT Pub. No.: WO2016/083520
PCT Pub. Date: Jun. 2, 2016

(65) Prior Publication Data
US 2017/0368342 A1 Dec. 28, 2017

(30) Foreign Application Priority Data
Nov. 27, 2014 (DE) .................. 10 2014 117 427

(51) Int. Cl.
*A61B 5/00* (2006.01)
*A61N 1/36* (2006.01)
(Continued)

(52) U.S. Cl.
CPC ........ *A61N 1/36014* (2013.01); *A61B 5/4082* (2013.01); *A61B 5/4094* (2013.01);
(Continued)

(58) Field of Classification Search
CPC .................. A61N 1/36175; A61N 1/36067
(Continued)

(56) References Cited

U.S. PATENT DOCUMENTS

2009/0319004 A1* 12/2009 Sabel .................. A61H 5/00
607/54
2012/0277820 A1* 11/2012 Wu .................. A61N 1/36067
607/45
(Continued)

FOREIGN PATENT DOCUMENTS

| DE | 10 2010 000 390 A1 | 8/2011 |
|----|----|----|
| DE | 10 2012 002 436 A1 | 8/2013 |
| WO | WO 2010/112023 A2 | 10/2010 |

OTHER PUBLICATIONS

A. N. Silchenko, I. Adamchic, C. Hauptmann, P.A. Tass: Impact of acoustic coordinated reset neuromodulation on effective connectivity in a neural network of phantom sound. NeuroImage 77, 133-147 (2013).

(Continued)

*Primary Examiner* — Amanda K Hulbert
*Assistant Examiner* — Philip C Edwards
(74) *Attorney, Agent, or Firm* — Arent Fox LLP (57) ABSTRACT

A device is provided for stimulating neurons that includes a non-invasive stimulation unit that generates stimuli in multiple stimulation channels. The stimulation unit generates the stimuli to stimulate a neuron population in the brain and/or spinal cord of a patient using the stimulation channels in different locations. Moreover, the device includes a control unit that controls the stimulation unit to repeatedly generates sequences of the stimuli with the order of the stimulation channels in which stimuli are generated within a sequence being constant for 20 or more successively generated sequences before it is varied.

19 Claims, 6 Drawing Sheets

(51) Int. Cl.
*A61N 2/00* (2006.01)
*A61M 21/00* (2006.01)
*A61B 5/0476* (2006.01)
*A61B 5/0478* (2006.01)
*A61B 5/0488* (2006.01)

(52) U.S. Cl.
CPC ......... *A61M 21/00* (2013.01); *A61N 1/36025* (2013.01); *A61N 1/36175* (2013.01); *A61B 5/0476* (2013.01); *A61B 5/0478* (2013.01); *A61B 5/0488* (2013.01); *A61B 5/4064* (2013.01); *A61B 5/4088* (2013.01); *A61B 5/4836* (2013.01); *A61B 2562/0219* (2013.01); *A61M 2021/0022* (2013.01); *A61M 2021/0027* (2013.01); *A61M 2021/0055* (2013.01); *A61M 2021/0066* (2013.01); *A61M 2021/0072* (2013.01); *A61N 1/361* (2013.01); *A61N 1/36064* (2013.01); *A61N 1/36067* (2013.01); *A61N 1/36082* (2013.01); *A61N 1/36103* (2013.01); *A61N 1/36139* (2013.01); *A61N 1/36178* (2013.01); *A61N 2/006* (2013.01)

(58) Field of Classification Search
USPC .......................................................... 607/72
See application file for complete search history.

(56) References Cited

U.S. PATENT DOCUMENTS

2013/0041296 A1   2/2013   Tass et al.
2015/0297444 A1   10/2015  Tass et al.

OTHER PUBLICATIONS

I. Adamchic, B. Langguth, C. Hauptmann, P.A. Tass: Abnormal cross-frequency coupling in the tinnitus network, Frontiers in Neuroscience 8, 284 (2014).

I, Adamchic, T. Toth, C. Hauptmann, P.A. Tass: Reversing pathologically increased EEG power by acoustic CR neuromodulation. Human Brain Mapping 35, 2099-2118 (2014).

P.A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159.

* cited by examiner

DEVICE AND METHOD FOR EFFECTIVE NON-INVASIVE NEUROSTIMULATION BY MEANS OF VARYING STIMULUS SEQUENCES

CROSS-REFERENCE TO RELATED APPLICATIONS

This application is a National Stage entry of International Application No. PCT/EP2015/077802, filed on Nov. 26, 2015, which claims priority to German Application No. 10 2014 117 427.5, filed on Nov. 27, 2014, the contents of each of these priority applications are hereby incorporated by reference in their entirety.

TECHNICAL FIELD

The invention relates to an apparatus and to a method for effective non-invasive neurostimulation by means of varying stimulus sequences.

BACKGROUND

Nerve cell assemblies in circumscribed regions of the brain are pathologically synchronously active in patients with neurological or psychiatric diseases such as Parkinson's disease, essential tremor, dystonia, functional disturbances after a stroke, migraine, obsessive compulsive disorders, epilepsy, tinnitus, schizophrenia, borderline personality disturbance and irritable bowel syndrome. In this case, a large number of neurons synchronously form action potentials, i.e. the participating neurons fire excessively synchronously. In a healthy person, in contrast, the neurons fire with a different quality, e.g. in an uncorrelated manner, in these brain areas.

In Parkinson's disease, the pathologically synchronous activity in the thalamus and in the basal ganglia changes the neuronal activity in other brain areas, e.g. in areas of the cerebral cortex such as the primary motor cortex. In this respect, the pathologically synchronous activity in the region of the thalamus and of the basal ganglia, for example, imposes its rhythm on the cerebral cortex areas such that ultimately the muscles controlled by these areas develop pathological activity, e.g. a rhythmic trembling (tremor). With chronically subjective tinnitus, pathological synchronous activity is found in a network of auditory and non-auditory brain areas.

In patients with brain diseases and spinal cord diseases that are characterized by excessively synchronized neuronal activity, non-invasively determined spatiotemporal stimulus patterns, in particular "coordinated reset" stimulation (CR stimulation) are applied to achieve permanent relief. The non-invasive CR stimulation can be implemented by means of different stimulation modes;

(i) by sensory stimulation, i.e. by physiological stimulation of receptors such as acoustic stimulation of the inner ear, visual stimulation of the retina or mechanical (e.g. vibrotactile) or thermal stimulation of receptors of the skin, hypoderm, muscles and sinews;
(ii) by stimulation of peripheral nerves (and associated receptors) e.g. by means of electric current (e.g. transcutaneous electrostimulation), by means of magnetic fields (transdermal magnetic stimulation) or by means of ultrasound; and
(iii) by stimulation of the brain or spinal cord e.g. by means of electric current (e.g. external cranial or transcranial neurostimulation), by means of magnetic fields (e.g. transcranial magnetic stimulation) or by means of ultrasound.

Acoustic CR stimulation is used to treat chronically subjective tonal or narrow-band tinnitus. For this purpose, therapeutic sounds are adapted to the dominant tinnitus tone and are applied in the sense of CR stimulation to achieve a long-lasting desynchronization of the pathologically synchronous activity or even a lasting desynchronization thereof that considerably survives the switching off of the stimulation. The acoustic CR stimulation for treating tinnitus effects a significant and considerably pronounced reduction of the symptoms (cf. P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012)), a significant reduction of pathological neuronal synchronization in a network of auditory and non-auditory brain areas (cf. P A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012); I. Adamchic, T. Toth, C. Hauptmann, P. A. Tass: Reversing pathologically increased EEG power by acoustic CR neuromodulation. Human Brain Mapping 35 2009-2118 (2014)), a significant reduction of the pathological interactions between different brain areas therein (cf. A. N. Silchenko, I. Adamchic, C. Hauptmann, P. A. Tass: Impact of acoustic coordinated reset neuromodulation on effective connectivity in a neural network of phantom sound. Neuroimage 77, 133-147 (2013)), as well as in different frequency ranges (cf. I. Adamchic, B. Langguth, C. Hauptmann, P. A. Tass: Abnormal brain activity and cross-frequency coupling in the tinnitus network. Frontiers in Neuroscience 8, 284 (2014)).

Parkinson's disease can be treated in an analog manner by means of vibrotactile CR stimulation. Further indications are e.g. represented by epileptic fits, functional disturbances after stroke, chronic pain syndromes (by means of vibrotactile and/or thermal CR stimulation), migraine (e.g. by means of visual CR stimulation). These diseases can furthermore be treated by transcranial magnetic stimulation or by direct electrical stimulation of the brain or direct brain stimulation by means of ultrasound.

All three of the above-named stimulation modalities (i) to (iii) have three substantial disadvantages named in the following:

a) The stimulation effect can vary relevantly from application to application, i.e. from stimulation epoch to stimulation epoch. In other words, the stimulation effect is dependent to a relevant degree on the initial conditions of the organism or nervous system in which the stimulation is started. If e.g. a very good effect is achieved in the one stimulation epoch, this effect will rather be unsatisfactory in a next stimulation epoch.
b) The stimulation success depends too greatly on the stimulus intensity in the previous form of the CR stimulation. Variations of the stimulus intensity can typically not be avoided in non-invasive CR stimulation. E.g. the patients in the acoustic CR stimulation for treating tinnitus adapt the intensity of the CR sounds to the volume of the environmental noise. In vibrotactile CR stimulation, the contact pressure and thus the stimulus intensity can e.g. depend on the base on which the patients support the stimulated extremity together with the vibrotactile actuators. Brightness fluctuations of the environment produce different stimulus strengths in the optical stimulation (e.g. by means of transmission eyeglasses). On the electrical stimulation of the skin, the stimulus strength depends on the conductivity of the skin and thus e.g. on the perspiration and generally on the vegetative state and overall status or heath status of the patient.

c) The stimulus strength must very generally be considered in relation to characteristic parameters of the system to be stimulated, that is of the body or of the nervous system. Since these parameters (e.g. specific ion concentrations, fluid volumes, hormone concentrations, etc.) fluctuate and are e.g. subject to pronounced fluctuations at different times of day, an optimum stimulus strength should either be correspondingly corrected or a stimulation method should be used whose stimulation effects are as independent as possible of these fluctuations.

In summary, the effect of the previously used CR stimulation is not sufficiently robust with respect to fluctuations of the stimulus intensity as well as with respect to characteristic parameters of the organism or nervous system to be stimulated (at the start of the stimulation as well as in the course of stimulation) and the effect of the CR stimulation in particular fluctuates by too much from stimulation epoch to stimulation epoch, i.e. there are too many stimulation epochs with a small effect.

SUMMARY

It is the underlying object of the invention to provide an apparatus and a method that allow improved, and in particular long-lasting, therapeutic effects to be achieved over a wide intensity range.

The object underlying the invention is satisfied by the features of the independent claims. Advantageous further developments and aspects of the invention are set forth in the dependent claims.

BRIEF DESCRIPTION OF THE DRAWINGS

The invention will be explained in more detail in the following in an exemplary manner with reference to the drawings. There are shown in these.

DETAILED DESCRIPTION

Figure 1:
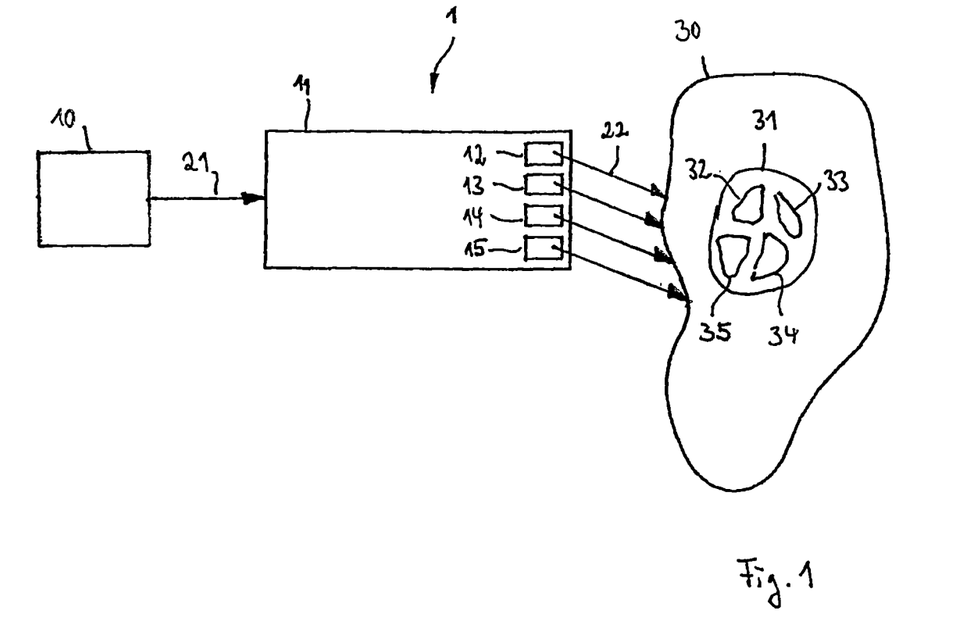
FIG. 1 illustrates a schematic representation of an apparatus for suppressing a pathologically synchronous and oscillatory neuronal activity and in particular for desynchronizing neurons having a pathologically synchronous and oscillatory activity in accordance with a first embodiment.

An apparatus 1 for stimulating neurons having a pathologically synchronous and oscillatory neuronal activity is shown schematically in FIG. 1. The apparatus 1 comprises a control unit 10 ad a stimulation unit 11 that stimulates neurons in the brain and/or spinal cord 30 of a patient over a plurality of stimulation channels. Each stimulation channel allows the stimulation of a different target area in the brain and/or spinal cord 30 of the patient, wherein the target areas associated with the stimulation channels do not necessarily have to be disjunctive, i.e. completely separated from one another, but can also overlap one another. The stimulation over four stimulation channels 12, 13, 14 and 15 is shown by way of example in FIG. 1. Stimulation can, however, naturally take place over a different number of stimulation channels.

During the operation of the apparatus 1, the control unit 10 carries out a control of the stimulation unit 11. For this purpose, the control unit 10 generates control signals 21 which are received by the stimulation unit 11.

The stimulation unit 11 generates stimuli 22 in the stimulation channels 12 to 15 using the control signals 21, said stimuli being administered to the patient. The stimuli 22 can be sensory stimuli, e.g. acoustic, visual, tactile, vibratory, thermal, olfactory, gustatory, transcutaneous electrical, transcutaneous magnetic and/or transcranial electrical and/or transcranial magnetic stimuli and/or ultrasound stimuli. Tactile and vibratory stimuli 22 are in particular also applied together and are then called vibrotactile stimuli 22. The stimuli 22 can in particular be consciously perceivable by the patient. The stimuli 22 are adapted to suppress the pathologically synchronous and oscillatory neuronal activity on administration to the patient over the stimulation channels 12 to 15 and in particular to desynchronize the neurons having the pathologically synchronous and oscillatory activity.

The stimulus unit 11 and in particular also the control and analysis unit 10 are non-invasive units, i.e. they are located outside the body of the patient during the operation of the apparatus 1 and are not surgically implanted in the body of the patient.

The apparatus 1 and the apparatus 2 described further below in connection with FIG. 3 can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neuronal synchronization.

The aforesaid diseases can be caused by a disorder of the bioelectrical communication of neuronal assemblies which are connected in specific circuits. In this respect, a neuronal population continuously generates pathological neuronal activity and possibly a pathological connectivity associated therewith (network structure). In this respect, a large number of neurons synchronously form action potentials, i.e. the participating neurons fire excessively synchronously. In addition, there is the fact that the pathological neuronal population has an oscillatory neuronal activity, i.e. the neurons fire rhythmically. In the case of neurological or psychiatric diseases, the mean frequency of the pathological rhythmic activity of the affected neuronal assemblies lies approximately in the range from 1 to 30 Hz, but can also be outside this range. In healthy people, the neurons fire qualitatively differently, however, e.g. in an uncorrelated manner.

The apparatus 1 is shown during a CR stimulation in FIG. 1. At least one neuronal population 31 in the brain and/or spinal cord 30 of the patient has a pathologically synchronous and oscillatory neuronal activity as described above. The stimulation unit 11 generates sensory stimuli 22 that are received by the patient and that are forwarded over the nervous system to the pathologically active neuronal population 31 in the brain and/or spinal cord 30. The stimuli 22 are designed such that the time-delayed (or phase-shifted) stimulation effects a desynchronization of the pathologically synchronous activity of the neuronal population 31 over at least two stimulation channels. A lowering of the coincidence rate of the neurons effected by the stimulation can result in a lowering of the synaptic weights and thus in an unlearning of the tendency to produce pathologically synchronous activity.

The stimuli 22 administered in the CR stimulation effect a reset of the phase of neuronal activity of the stimulated neurons in the neuronal population 30. The phase of the stimulated neurons is set to or close to a specific phase value, e.g. 0°, independently of the current phase value by the reset (it is not possible in practice to set a specific phase value exactly; however, this is also not required for a successful CR stimulation). The phase of the neuronal activity of the pathological neuronal population 31 is thus controlled by means of a direct stimulation. Since the pathological neuronal population 31 is stimulated at different points over the stimulation channels 12 to 15, the phases of the neuronal activity of the subpopulations 32 to 35 of the pathological neuronal population 31 shown in FIG. 1 can be reset at different points in time in that the stimuli 22 are applied in a time-delayed (or phase-shifted) manner over the stimulation channels 12 to 15. As a result, the pathological neuronal population 31 whose neurons were previously active synchronously and at the same frequency and phase are thereby split into a plurality of subpopulations having different phases. For example, the subpopulation 32 is stimulated over the stimulation channel 12; the subpopulation 33 is stimulated over the stimulation channel 13; the subpopulation 34 is stimulated over the stimulation channel 14; and the subpopulation 35 is stimulated over the stimulation channel 15. The neurons are still synchronous and also still fire at the same pathological frequency within each of the subpopulations 32 to 35 after the end of the phase; however, each of the subpopulations 32 to 35 has that phase with respect to its neuronal activity that was imparted on it by the stimulus 22 generated in the respective stimulation channel 12 to 15. This means that the neuronal activities of the individual subpopulations 32 to 35 still have an approximately sinusoidal curve at the same pathological frequency, but different phases, after the resetting of their phases.

Due to the pathological interaction between the neurons, the state with at least two subpopulations generated by the stimulation is unstable and the total neuronal population 31 fast approaches a state of complete desynchronization in which the neurons fire without correlation. The desired state i.e. the complete desynchronization is thus not immediately present after the time-delay (or phase-shifted) application of the stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It also has the effect that a division of an overall population 31 into subpopulations 32 to 35 with different phases is followed by a desynchronization. In contrast to this, no desynchronization would take place without a pathologically increased interaction of the neurons.

Furthermore, a reorganization of the connectivity of the disturbed neuronal networks can be achieved by the CR stimulation so that long-continuing therapeutic effects can be brought about. The obtained synaptic conversion is of great importance for the effective treatment of neurological or psychiatric diseases.

Figure 2A:
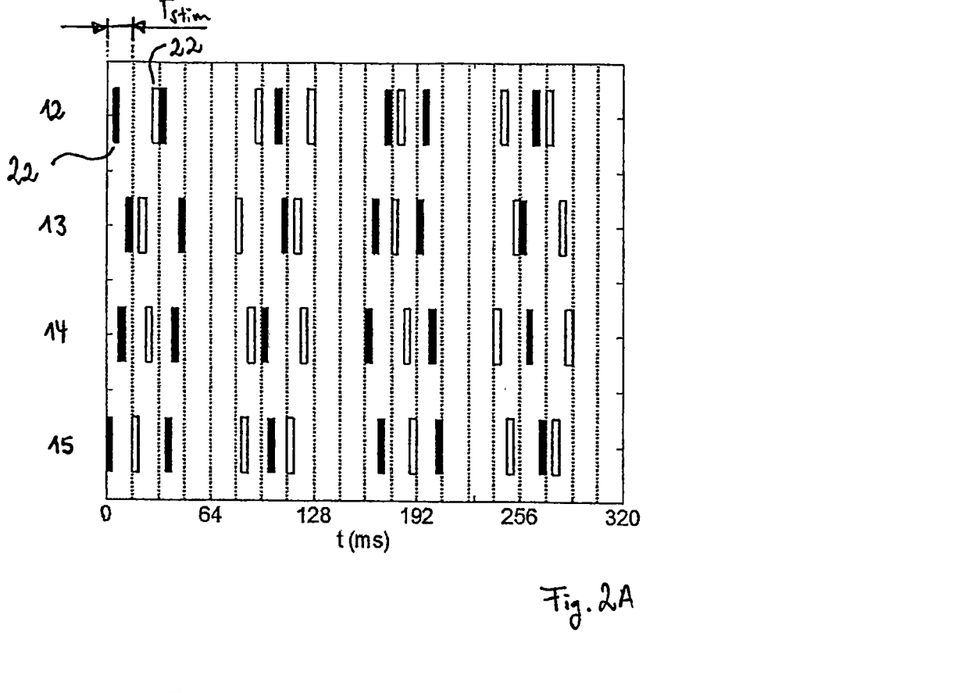
FIG. 2A illustrates a schematic representation of a CR stimulation with fast-varying stimulus sequences.

FIG. 2A shows a CR stimulation in which sequences of stimuli 22 are generated repetitively in four stimulation channels 12 to 15. The stimuli 22 generated in the stimulation channels 12 to 15 are applied among one another against the time t in FIG. 2A. The sequences are generated in a predefined time pattern that comprises consecutive cycles. The individual cycle are delineated from one another by dashed lines in FIG. 2A. Each cycle has the length $T_{stim}$. In each cycle in which a stimulation takes place, exactly one sequence of stimuli 22 is generated in the stimulation channels 12 to 15 together and exactly one stimulus 22 is generated in each stimulation channel 12 to 15, i.e. each sequence in the present example comprises a progression of four time-delayed stimuli 22 that are in particular generated in respectively different stimulation channels 12 to 15, wherein the time delay can in particular relate to the starting times of the stimuli 22. At the start of each cycle, the order of the stimulation channels 12 to 15 in which the stimuli 22 are generated within the respective sequence is varied in the present example. A different filling of the bars shown in FIG. 2A that symbolize the stimuli 22 shows a variation of the order. For example, the stimuli 22 are generated in the order 15-12-14-13 in the stimulation channels 12 to 15 in the first cycle shown in FIG. 2A. The order in the second cycle is 15-13-14-12 and the order in the third cycle is 12-15-14-13.

Furthermore, in the exemplary stimulation form shown in FIG. 2A, stimuli 22 are always applied in three consecutive cycles and then a break in which no stimuli 22 are generated is observed for two cycles. This pattern is periodically repeated.

Figure 2B:
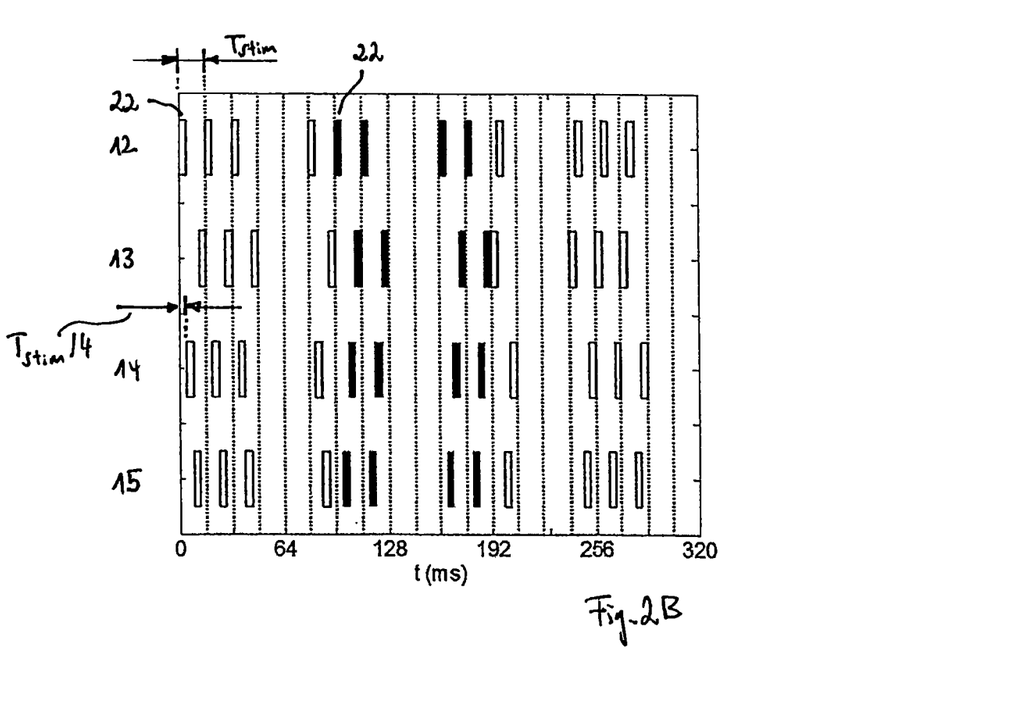
FIG. 2B illustrates a schematic representation of a CR stimulation with slowly varying stimulus sequences.

FIG. 2B shows a further development of the CR stimulation of FIG. 2A. The main difference from the stimulation in accordance with FIG. 2A is that the sequences are only varied very slowly in the CR stimulation shown in FIG. 2B. Provision is in particular made that the order of the stimulation channels 12 to 15 in which the stimuli 22 are generated within a sequence is kept constant for at least 20 sequences generated after one another and is only varied afterward. A CR stimulation using such slowly varying sequences is considerably superior with respect to the CR stimulation shown in FIG. 2A since its desired, i.e. therapeutic, stimulation effect (i) is more pronounced; (ii) varies much less from stimulation epoch to stimulation epoch; and (iii) is considerably more robust with respect to fluctuations of the stimulus intensity; with respect to fluctuations of characteristic parameters of the body or of the nervous system; and in particular with respect to variations of the initial values.

It is generally known that the repetition of the content to be learned plays an important role during learning. The invention utilizes the surprising relationship that the repetition is also of very high importance in the unlearning. I.e. to unlearn pathologically synchronous synaptic links and thus pathologically synchronous neuronal activity considerably better, the sequences of the CR stimulation should only be varied slowly so that every individual sequence is repeated frequently enough.

Provision can be made, as described above, that the sequences remain the same for at least 20 sequences generated after one another and are only changed afterward. It is furthermore conceivable to increase the repetition of the same sequence and to keep constant the order of the stimulation channels 12 to 15 in which the stimuli 22 are generated within a sequence for at least 25 or at least 30 consecutively generated sequences. It must again be pointed out at this point that the sequences are already varied after fewer than 20 consecutively generated sequences in FIG. 2B for reasons of illustration. This is, however, only to be understood as a simplified representation of a sequence variation that is slow in comparison with FIG. 2A.

In accordance with an embodiment, only the order of the stimulation channels 12 to 15 in which the stimuli 22 are generated within a sequence is varied in the CR stimulation shown in FIG. 2B. All the other stimulation parameters can remain constant during the CR stimulation.

The variation of the sequences can e.g. take place stochastically or deterministically or in a mixed stochastic-deterministic manner.

Exactly as in FIG. 2A, cycles can also be provided in the CR stimulation in accordance with FIG. 2B in which stimulation breaks are observed. Stimuli 22 can thus be generated during n consecutive cycles and, during the following m cycles, no stimuli 22 are generated that are designed to suppress the pathologically synchronous and oscillatory neuronal activity, where n and m are non-negative whole numbers. It is, however, conceivable that different stimuli that are not adapted to suppress pathologically synchronous and oscillatory neuronal activity are applied during the stimulation breaks, in particular using the stimulation unit 11. Provision can furthermore be made that the stimulation unit 11 does not generate any stimuli during the stimulation breaks. The pattern of n cycles with stimulation and m cycles without stimulation can be periodically continued.

Provided that provision is made to vary the sequences after a predefined number i of consecutively generated sequences (i≥20), in accordance with an embodiment, the cycles without any stimulation are not counted, i.e. in this embodiment, a variation of the order of the stimulation channels 12 to 15 only takes place when a respective sequence of stimuli 22 was actually applied in i cycles. The number i according to which the sequence is respectively varied, can e.g. be determined in accordance with stochastic or deterministic or mixed stochastic-deterministic rules.

The variation of the sequences can furthermore take place with a constant rhythm, i.e. a variation always takes place, for example, after i cycles.

A respective one of the subpopulations 32 to 34 of the pathological neuronal population 31 shown in FIG. 1 is stimulated over each of the four stimulation channels 12 to 15. During the at least 20 cycles in which the sequences are constant, the stimulus 22 is periodically applied with the period $T_{stim}$ over each of the four stimulation channels 12 to 15. The stimuli 22 effect a phase reset of the neuronal activity of the respective stimulated subpopulation. The time delay between stimuli 22 generated directly after one another in time in different stimulation channels within a sequence furthermore amounts to $T_{stim}/4$ since, in the present embodiment, the stimuli 22 are generated in four stimulation channels 12 to 15. For the general case of P stimulation channels used for the stimulation, the time delay between stimuli 22 generated directly after one another in time in different stimulation channels within a sequence would amount to $T_{stim}/P$ (a deviation from this value by e.g. up to ±5%, ±10% or ±20% is also possible). The time delay $T_{stim}/P$ can relate to the initial points in time of the stimuli 22. The stimuli 22 generated in different stimulation channels can be identical except for the different starting times.

The period $T_{stim}$ that indicates the duration of a cycle, on the one hand, and the period with which unchanging sequences and the stimuli 22 generated in a respective stimulation channel 12 to 15, on the other hand, can be close to the mean period of the pathological oscillation of the neuronal population 31 having the pathologically synchronous and oscillatory neuronal activity or can differ from the mean period by up to ±5%, ±10% or ±20%. The frequency $f_{stim}=1/T_{stim}$ is typically in the range from 1 to 30 Hz. The period of the pathological oscillation of the neuronal population 31 to be stimulated can be measured, for example, by means of the measuring unit 16 described below, in particular by means of EEG.

It is, however, also possible to use text book values or empirical values that relate to the respective disease to be treated for the period of the pathological oscillation.

The phase-resetting stimuli 22 can, for example, be individual stimuli or also assembled stimuli. Each stimulus 22 can, for example, comprise a pulse train of 1 to 100, in particular 2 to 10, individual pulses. The individual pulses within a pulse train are repeated without interruption at a frequency in the range from 50 to 500 Hz, in particular in the range from 100 to 150 Hz. Depending on the kind of stimulation, it can be an acoustic, visual, tactile, vibratory (in particular vibrotactile), thermal, olfactory, gustatory, transcutaneous electrical, transcutaneous magnetic, transcranial electrical and/or transcranial magnetic pulse train and/or an ultrasound pulse train.

It can generally be possible to have stimulation by means of the stimulation unit 11 over any desired number L of stimulation channels (L≥2); however, all the stimuli 22 do not necessarily have to be generated in all L stimulation channels in a stimulation; it is also possible, for example, to generate the stimuli 22 only in a selection P of the L stimulation channels (2≤P≤L). With P stimulation channels, P! possible different sequences result, wherein exactly one stimulus 22 is generated in each of the P stimulation channels in each of these sequences. It is conceivable to use all P! possible sequences for the stimulation or also to select a subset for the stimulation from the set of P! possible sequences. This subset can also vary in time in accordance with stochastic or deterministic or mixed stochastic-deterministic rules. The progression of the sequences can be random or can also be fixed before or also during the stimulation.

The apparatus 1 shown in FIG. 1 for stimulating neurons having a pathologically synchronous and oscillatory neuronal activity carries out a so-called "open-loop" stimulation, i.e. a stimulation without sensors that are used for feedback and/or for control of the stimulation.

Figure 3:
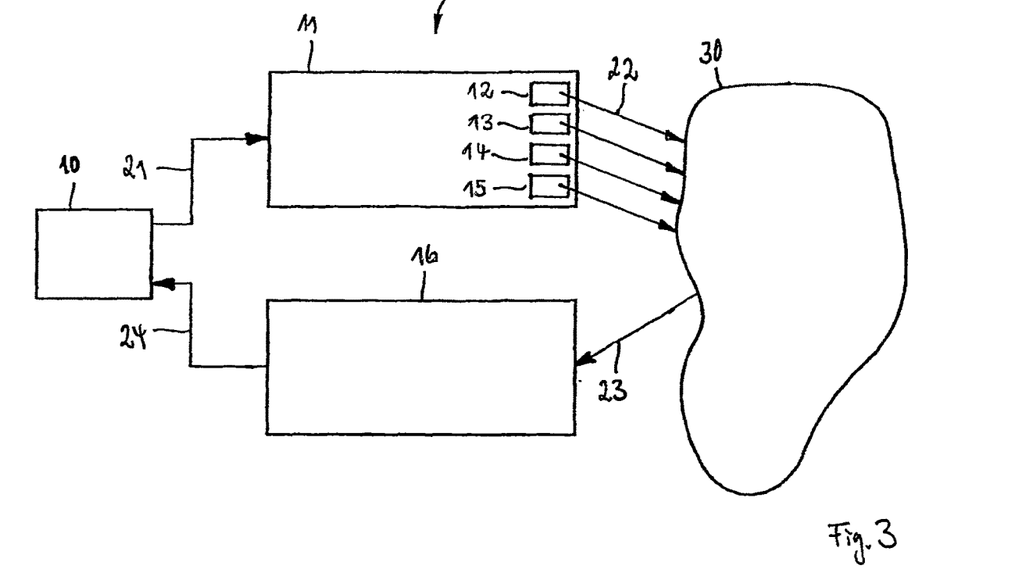
FIG. 3 illustrates a schematic representation of an apparatus for suppressing a pathologically synchronous and oscillatory neuronal activity and in particular for desynchronizing neurons having a pathologically synchronous and oscillatory activity in accordance with a second embodiment.

FIG. 3 schematically shows an apparatus 2 for stimulating neurons having a pathologically synchronous and oscillatory neuronal activity with which a closed-loop stimulation can be carried out. The apparatus 2 is a further development of the apparatus 1 shown in FIG. 1 and, exactly like the apparatus 1, includes a control unit 10 and a non-invasive stimulation unit 11 that have the same functions as the above-described control and stimulation units 10, 11 of the apparatus 1.

The apparatus 2 furthermore comprises a measuring unit 16. The stimulation effect achieved by the stimuli 22 is measured with the aid of the measuring unit 16. The measuring unit 16 records one or more measured signals 23 measured at the patient, converts them as required into electrical signals 24 and supplies them to the control unit 10. The neuronal activity in the stimulated target zone or in a zone associated with the target zone can in particular be measured by means of the measuring unit 16, with the neuronal activity of this zone correlating sufficiently closely with the neuronal activity of the target zone. A non-neuronal activity, e.g. a muscular activity, or the activation of the autonomous nervous system can also be measured by means of the measuring unit 16 provided that they are sufficiently closely correlated with the neuronal activity of the target region.

The measuring unit 16 includes one or more sensors that in particular make it possible to demonstrate a decrease or increase in the amplitude of the pathological oscillatory activity.

Non-invasive sensors can be used as the sensors, e.g. chronically or intermittently used electroencephalography (EEG) electrodes or electromyography (EMG) electrodes or magnetoencephalography (MEG) sensors. The neuronal activity can also be determined by detection of characteristic movement patterns such as tremor, akinesia, or epileptic fits with the aid of an accelerometer or gyroscope or indirectly by measuring the activation of the autonomous nervous system by means of a measurement of the skin resistance. Mental state values that can be input into portable devices, e.g. smartphones, by the patient can also be used to monitor the stimulation success.

Alternatively, but less preferably, the sensors can be implanted in the body of the patient. Epicortical electrodes, deep brain electrodes for the measurement of e.g. local field potentials, subdural or epidural brain electrodes, subcutaneous EEG electrodes and subdural or epidural spinal cord electrodes can, for example, serve as invasive sensors.

The control unit 10 processes the signals 24, e.g. the signals 24 can be amplified and/or filtered, and analyzes the processed signals 24. The control unit 10 checks the stimulation success using the measured signals recorded in response to the application of the stimuli 22.

In accordance with an embodiment, the sequences generated by the stimulation unit 11 are varied with a constant rhythm, i.e. the order of the stimulation channels 12 to 15 in which the stimuli 22 are generated per sequence is kept constant for a predefined number of cycles (at least 20) and the order is varied afterward. The order is subsequently again kept constant for the predefined number of cycles and is varied afterward. This pattern is correspondingly continued. In this embodiment, the rhythm with which the sequences are varied remains constant and is in particular not adapted to the measured signals 23 processed by the control unit 10 however, as required, other stimulation parameters such as the amplitude of the stimuli 22 can be set in dependence on the measured signals 23.

The above embodiment can be further developed in that the rhythm of the sequences is set in dependence on the processed measured signals 23. The control unit 10 checks the stimulation success using the measured signals 23 recorded in response to the application of the stimuli 22 and sets the stimulation parameters, in particular the rhythm with which the stimulation sequences are varied, in dependence on the stimulation success.

The stimulation success can in particular be checked by means of a threshold value comparison. Depending on which signals are used for determining the stimulation success, different threshold value comparisons result. If e.g. the pathologically neuronal synchronization is measured via the sensors of the measuring unit 16, e.g. EEG electrodes, experience has shown that the lowering of the synchronization by e.g. at least 20% in comparison with the situation without stimulation is sufficient to determine a sufficient stimulation success. In accordance with an embodiment, an insufficient stimulation success can be determined if the pathologically neuronal synchronization by the application of the stimuli 22 is not reduced by at least a predefined value. If symptoms of the patient are used for determining the stimulation success, which reduction is to be considered as a clinically relevant improvement depends on the kind of clinical parameters used. Such reduction values (e.g. in the sense of the so-called minimal clinically perceptible improvement) are familiar to the skilled person.

If the CR stimulation in accordance with a threshold comparison is not sufficiently effective, i.e. a disease-specific marker does not reduce by a predefined threshold value in comparison with the balance state or with a starting/initial value, the number of repetitions of the same sequence is extended. If the stimulation is in contrast successful in accordance with the threshold value criterion, the number of repetitions of the same sequence is shortened. In the simplest case, this can be a binary switching between two values of the number of repetitions of the same sequence: e.g. 25 repetitions with a successful stimulation; in contrast, e.g. 100 repetitions with an unsuccessful stimulation. The demand-controlled number of repetitions of the same sequence can, however, also be varied/parameterized in smaller steps.

The individual components of the apparatus 1 and 2, in particular the control unit 10, the stimulation unit 11 and/or the measuring unit 16, can be separate from one another in a construction aspect. The apparatus 1 and 2 can therefore also be understood as systems. The control unit 10 can include e.g. a processor, e.g. a microcontroller, for carrying out its work. The stimulation processed described herein can be stored as software code in a memory associated with the control unit 10.

Figure 4:
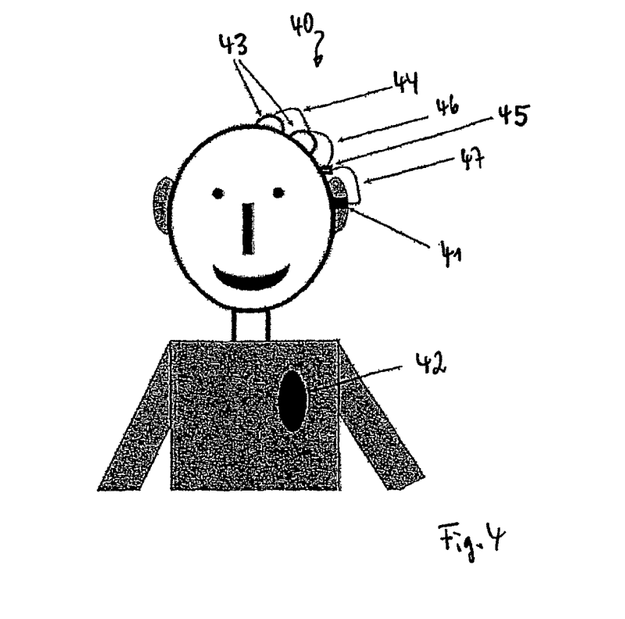
FIG. 4 illustrates a schematic illustration of an apparatus for the acoustic stimulation of neurons having a pathologically synchronous and oscillatory neuronal activity.

FIG. 4 schematically shows an apparatus 40 for non-invasive acoustic stimulation of neurons having a pathologically synchronous and oscillatory neuronal activity in accordance with an embodiment of the invention. Acoustic stimuli, in particular acoustic CR stimuli, are administered to the patient via earphones or headphones 41 or via loudspeakers of a different design with an earphone being a loudspeaker positioned in the ear canal. The control signals used for this purpose are generated by a control unit 42. Non-invasively fixed EEG electrodes 43 that are connected via a cable 44 serve for the closed loop stimulation. The corresponding calculation is carried out in a small component 45 that preferably contains a measurement amplifier and is connected to the EEC electrodes 43 or to the earphones or headphones 41 via cables 46, 47 and/or is carried out in the actual control unit 42 accommodating the battery or the rechargeable battery. The control unit 42 and the component 45 are connected to one another telemetrically in the embodiment shown in FIG. 4; in this case, the component 45 (or a component connected to it via cable) likewise contains a battery or a rechargeable battery. Alternatively, the control unit 42 and the component 45 can also be connected to one another via cable such that the component 45 is fed via the power supply of the control unit 42.

Figure 5:
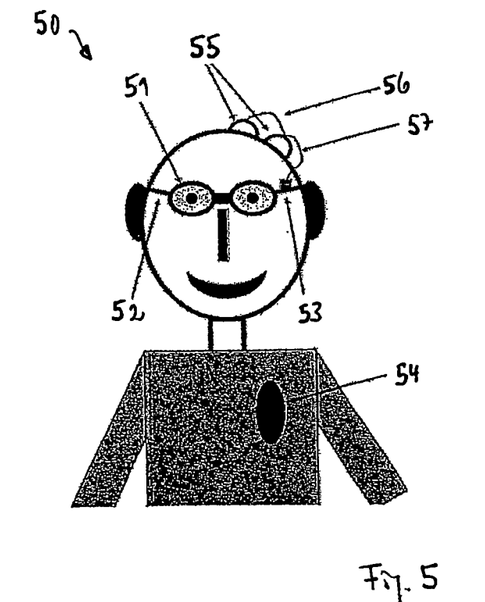
FIG. 5 illustrates a schematic illustration of an apparatus for the visual stimulation of neurons having a pathologically synchronous and oscillatory neuronal activity.

FIG. 5 schematically shows an apparatus 50 for non-invasive visual stimulation of neurons having a pathologically synchronous and oscillatory neuronal activity in accordance with an embodiment of the invention. In this embodiment, the patient wears stimulation eyeglasses 51 that are e.g. fastened to the head of the patient via a clamp 52. A component 53 contains a calculation and telemetry unit. The latter serves for the connection to the actual control unit 54 accommodating the battery or the rechargeable battery. The component 53 and the control unit 54 are telemetrically connected to one another; in this case, the component 53 (or a component connected to it via cable) likewise contains a battery or a rechargeable battery. Alternatively, the component 53 and the control unit 54 can also be connected to one another via cable. Non-invasively fixed EEG electrodes 55 serve for the closed loop stimulation. The EEG electrodes 55 are connected to the component 53 via cables 56, 57.

The visual stimuli 51 generated by the stimulation eyeglasses can have an underlying luminosity variation or brightness variation (or variation of the light intensity or luminosity); for example, they can be applied as pulses or as sequences of pulses with varied luminosity or brightness. The visual stimuli can be administered depending on the embodiment as luminosity modulation of natural visual stimuli, e.g. by means of homogenous or segmented transmission eyeglasses in which the transmission can be regulated independently of the voltage, as a modulated visual stimulus occurring in addition to a natural visual stimulus, e.g. by means of partially transparent light eyeglasses or as an artificial visual brightness stimulus, e.g. by means of opaque light eyeglasses. The stimulation eyeglasses 51 are preferably divided into different segments whose luminosity or transmission or brightness can be controlled separately to be able to stimulate different points of the retina independently of one another.

Figure 6:
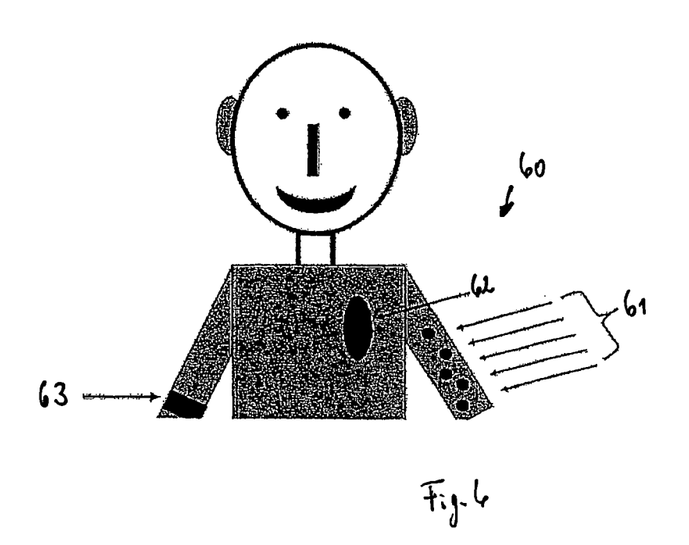
FIG. 6 illustrates a schematic representation of an apparatus for the tactile, vibratory, thermal, transcutaneous electrical and/or transcutaneous magnetic stimulation and/or ultrasound stimulation of neurons having a pathologically synchronous and oscillatory neuronal activity.

FIG. 6 schematically shows an apparatus 60 for the non-invasive tactile, vibratory, thermal, transcutaneous electrical and/or transcutaneous magnetic stimulation and/or for the ultrasound stimulation of neurons having a pathologically synchronous and oscillatory neuronal activity in accordance with an embodiment of the invention. The apparatus 60 comprises a stimulation unit 61, a control unit 62 controlling the stimulation unit 61, and an accelerometer 63 for recording measured signals. The stimulation unit 61 and the accelerometer 63 can be connected to the control unit 62 telemetrically or via cable.

The stimulation unit 61 comprises a plurality of stimulation elements for generating tactile, vibratory, thermal, transcutaneous electrical and/or transcutaneous magnetic stimuli and/or ultrasound stimuli. The stimulation elements are designed such that they can be placed on the skin of the patient. Depending on the disease and/or on the effected parts of the body, the stimulation elements are secured on the skin of the patient in a suitable arrangement, for example to the arm, to the leg, to the hand and/or to the foot of the patient. The plurality of stimulation elements make it possible to stimulate different receptive regions of the skin via the individual stimulation elements with time and space coordination.

Stimulation elements for generating tactile and/or vibratory stimuli are, for example, vibration actuators that press into the skin of the patient at a frequency in the range from 1 to 300 Hz, and in particular 1 to 60 Hz, and preferably 100 to 300 Hz, and thereby generate the desired stimuli. Stimulation elements for generating thermal stimuli can, for example, be lasers or elements of different designs for generating heat, in particular thermal heat. Electrodes are typically attached to the skin of the patient for generating transcutaneous electrical stimuli. Transcutaneous magnetic stimuli can be generated by corresponding stimulation elements for generating magnetic stimuli, in particular live coils. Ultrasound stimuli are generated by stimulation elements for generating ultrasound waves.

On the application of acoustic or visual stimuli, they are received via at least one ear or at least one eye of the patient. The tactile, vibratory, thermal, transcutaneous electrical and/or transcutaneous magnetic stimuli and/or ultrasound stimuli can be received by receptors disposed in or under the skin and can be forwarded to the nervous system. These receptors include, for example, Merkel cells, Ruffini corpuscles, Meissner's corpuscles and hair follicle receptors which in particular act as receptors for the tactile stimuli. The vibratory stimuli are predominantly directed to deep sensibility. The vibratory stimuli can be received by receptors disposed in the skin, in the muscles, in the subcutaneous tissue and/or in the sinews of the patient. Pacini's corpuscles, which communicate vibration perceptions and accelerations, can be named as examples for the vibration stimuli. The thermal stimuli are received by the thermoreceptors of the skin. They are warm receptors (also called heat receptors, warm sensors or heat sensors) and cold sensors (also called cold receptors). The cold sensors are more superficial in the skin of people; the heat receptors somewhat lower. The transcutaneous electrical and transcutaneous magnetic stimuli as well as the ultrasound stimuli do not act specifically on only one group of receptors disposed in or beneath the skin and can furthermore also directly stimulate nerve fibers.

The directed stimulation of specific regions of the brain or spinal cord is made possible by the tonotopic or somatotopic association of body regions with these regions. For example, acoustic stimuli are converted into nerve impulses in the inner ear and are forwarded via the acoustic nerve to the auditory cortex. A specific portion of the auditory cortex is activated on the acoustic stimulation of the inner ear at a specific frequency due to the tonotopic arrangement of the auditory cortex.

On the visual stimulation, different points in the visual field are imaged on different points of the retina via the crystalline lens of the eye. The different points of the retina are in turn connected via the optic nerve to different neurons in the brain. Consequently, respective different neurons can be stimulated using the stimuli applied at different spatial sites.

Due to the somatotopic structuring of the neural pathways and of the associated zones of the brain, different neurons are furthermore stimulated by tactile, vibratory, thermal, transcutaneous electrical and/or transcutaneous magnetic stimuli and/or ultrasound stimuli which are applied at different points on the skin. With these types of stimulation, the stimulation elements can be attached, for example, to the foot, lower leg and upper leg or to the hand, the lower arm and upper arm of the patient in order thereby to be able to stimulate specific neurons.

On a gustatory stimulation, different areas of the tongue are stimulated by the corresponding gustative qualities—sweet, sour, salt, bitter and umami (Japanese for savory, spicy, brothy aroma). It is, however, also possible to stimulate the tongue electrically. In this case, primarily the mucous membrane is stimulated that activates a substantially large representation, i.e. a substantially large associated area, in the cortical homunculus (physical representation of the human body in the sensory and motor cortex). Due to the somatotopic structure of the neural pathways and associated brain areas, different neurons are stimulated by gustatory stimuli that are applied at different points of the tongue.

The following applies very generally and not only in relation to the embodiments described here: In the acoustic stimulation, each stimulation channel is associated with a respective different frequency range from which the sounds that are applied as acoustic stimuli in the respective stimulation channel are selected. In the visual stimulation, the stimulation channels are determined by different points or regions in the visual field of the patient. The visual stimuli generated in a respective stimulation channel are generated at a respective point or in a respective region of the visual field. The stimulation channels of the tactile, vibratory, thermal, transcutaneous electrical and/or transcutaneous magnetic stimuli and/or ultrasound stimuli are determined by the points of the skin that are stimulated by the respective stimulation elements. Consequently each stimulation channel is associated with a respective point or with a respective region of the skin.

The stimulation channels of the gustatory stimuli are determined by the points of the tongue that are stimulated by the corresponding gustatory qualities or electrical stimuli. In an olfactory stimulation, psychophysically sufficiently disjunctive olfactory stimuli are used by which the stimulation channels are determined. The psychophysically sufficiently disjunctive olfactory stimuli could e.g. be personalized, i.e. adapted to the individual patient.

In the transcranial electrical and transcranial magnetic stimulation, electrodes or magnetic field generators, in particular live coils, are attached to the body, in particular to the head, of the patient. Currents or magnetic fields in the brain and/or spinal cord of the patient can be generated by the electrodes and magnetic field generators. Different target areas in the brain and/or spinal cord can be stimulated in dependence on the attachment site of the electrodes or magnetic field generators. The stimulation channels are consequently determined by the points at the body of the patient to which the electrodes or magnetic field generators are attached.

The stimulation unit described above can accordingly separately stimulate different regions of the brain or spinal cord over different stimulation channels in that the applied stimuli are forwarded via neural conductors to different target zones which lie in the brain and/or spinal cord. The target zones can be stimulated with possibly different and/or time-delayed stimuli during the stimulation.

As described above, the stimuli 22 effect a reset of the phase of the neuronal activity of the stimulated neurons in the CR stimulation. The phase reset of the individual stimuli 22 can be checked with the aid of the measured signals 23 recorded by the measuring unit 16. Such an examination can be carried out before the actual therapeutic neurostimulation.

For this purpose, a signal that sufficiently represents the activity of the subpopulation stimulated over the jth stimulation channel is measured via a sensor of the measuring unit 16. This signal is obtained either directly from the subpopulation via a non-invasive measurement, e.g. via EEG or MEG electrodes, or via an invasive measurement, e.g. implanted electrodes, as a surface EEG or as a local field potential via deep electrodes. The signal can also be determined indirectly via the measurement of a value correlated with the activity of the stimulated subpopulation. EEG/MEG/LFP signals of the neuronal activity of another neuronal population closely coupled to this subpopulation are e.g. suitable for this purpose or associated electromyography signals, accelerometer signals or gyroscope signals.

Since neuronal signals typically include rhythmic activity in different frequency bands, it is advantageous in such cases to determine the signal $x_j(t)$ that represents the pathological oscillatory activity of the subpopulation stimulated by the jth stimulation channel, e.g. by means of band pass filtering or wavelet analysis or empirical mode decomposition.

A procedure that is only a little complex to check a phase reset comprises determining the averaged stimulus response. A stimulus having identical stimulus parameters is applied at the times $\tau_1, \tau_2, \ldots, \tau_l$ for this purpose. The intervals between the individual stimuli $\tau_{k+1} - \tau_k$ should be sufficiently large and randomized, that is should not be constant, in order to avoid transient effects (cf. P A. Tass: Transmission of stimulus-locked responses in two coupled phase oscillators. Phys. Rev. E 69, 051909-1-24 (2004)). The intervals $\tau_{k+1} - \tau_k$ should typically be in the range of at least tenfold, preferably a hundredfold the mean period of the pathological oscillation. The stimulus response averaged over all l test stimuli is calculated in accordance with the following equation:

$$\bar{x}_j(t) = \frac{1}{l} \sum_{k=1}^{l} x_j(\tau_k + t) \tag{1}$$

Provided that the intervals $\tau_{k+1} - \tau_k$ between the individual stimuli are sufficiently large, no averaged stimulus response is obtained in the pre-stimulus range, i.e. in the range before the application of a respective stimulus (cf. P A. Tass: Transmission of stimulus-locked responses in two coupled phase oscillators. Phys. Rev. E 69, 051909-1-24 (2004)). A phase reset can be determined when an averaged stimulus response can be detected, i.e. when a stimulus response different from zero is found in the post-stimulus range, i.e. in the range for t>0, where t=0 represents the starting time of the respective stimulus. This can be determined by a visual inspection. It can also be carried out by the apparatus 2, in particular by the control unit 10, in that the pre-stimulus distribution of $\bar{x}_j(t)$ or $|\bar{x}_j(t)|$ is observed and a characteristic threshold value is determined, e.g. the 99th percentile of the pre-stimulus distribution of $|\bar{x}_j(t)|$ or simply its maximum. If now e.g. the amount of the post-stimulus response exceeds this characteristic threshold value in principle or for a predefined minimum time, e.g. 20 ms, an averaged response different from zero is present. A phase reset can be present in this case. I.e. the stimulus strength would have to be increased so much until the post-stimulus response differs from a zero line. In addition to the method presented here that is simple, but has been proven in practice, other statistical tests known to the skilled person can be used for the signal analysis.

A more exact, but more complex, variant for investigating whether the stimuli effect a phase reset is offered by the analysis of the phase. The phase $\psi_j(t)$ of $x_j(t)$ is determined for this purpose. This is done by means of a Hilbert transformation from the signal that represents the pathological oscillatory activity that is determined by means of band pass filtering or empirical mode decomposition. The empirical mode decomposition allows, in contrast to band pass filtering, a parameter-independent determination of physiologically relevant modes in different frequency ranges (cf. N. E. Huang et al.: The empirical mode decomposition and the Hilbert spectrum for nonlinear and non-stationary time series analysis. Proc. R. Soc. A: Math. Phys. Eng. Sci. 454:903-995 (1998)). The combination of empirical mode decomposition with a subsequent Hilbert transformation is called a Hilbert-Huang transformation (cf. N. E. Huang et al.: A confidence limit for the empirical mode decomposition and Hilbert spectral analysis, Proceedings of the Royal Society of London Series A, 459, 2317-2345 (2003)). The phase $\psi_j(t)$ can also be determined by means of wavelet analysis.

A phase reset is present when the phase $\psi_j(t)$ is set to a preferred value by a stimulus (at a stimulus start at t=0) after a specific time. I.e. $\{\psi_j(\tau_k+t)\}_{k=1,\ldots,l}$ the distribution of the values of the phase $\psi_j(t)$ acquired from the l stimulus responses has an accumulation point at the time t (relative to the burst start at t=0). The skilled person is aware of different methods with which it can be demonstrated that a distribution has an accumulation value (that is a peak). A common method is the determination of the phase reset index $\rho(t)$ by means of a circular mean value.

$$\rho(t) = \left| \frac{1}{l} \sum_{k=1}^{l} \exp[i\psi_j(\tau_k + t)] \right| \quad (2)$$

A phase reset is present when $\rho(t)$ e.g. exceeds the maximum or the 99th percentile of the pre-stimulus distribution of $\rho(t)$ (at a point in time or within a small time window of e.g. 20 ms width).

The analysis using the averaged responses $\bar{x}_j(t)$ has proved itself sufficiently in practice.

The effects achievable using the invention described herein are illustrated with reference to stimulation results in FIGS. 7 to 9. The simulation is based on a network of 200 neurons, wherein all the neurons have a highly exciting short-range coupling and a weak inhibitory long-range coupling among one another. The synaptic coupling strengths in the network can change in accordance with STPD (spike timing dependent plasticity) rules. An initially strongly coupled network produces highly synchronous neuronal activity.

The simulation is based on the following conditions. The CR stimulation starts at t=0 s and ends at t=64 s. Each cycle lasts 16 ms. A pattern of 3 cycles with stimulation and 2 cycles without stimulation is periodically repeated. The activity of the network is examined up to t=128 s, i.e. until 64 s after the end of the stimulation. The degree of synchronization S can be in the range from 0 (for a complete desynchronization) up to 1 (for a complete phase synchronization).

Figures 7A, 7B:
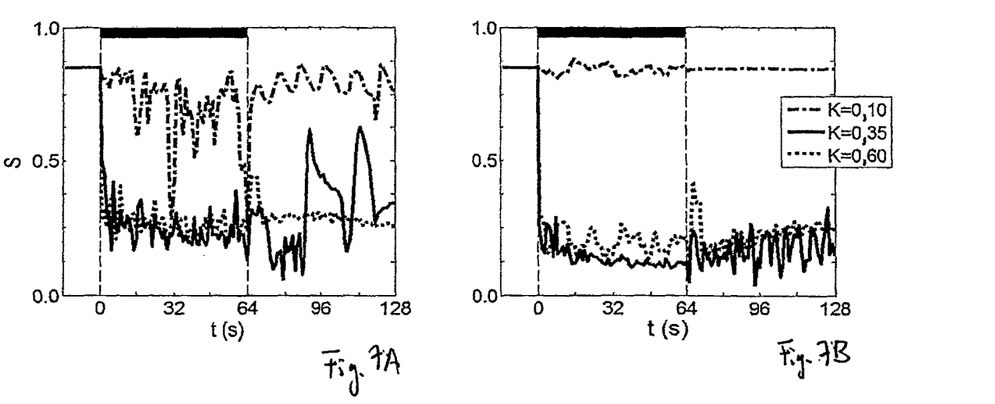
FIGS. 7 to 9 illustrate diagrams with simulation results for fast-varying and slowly varying CR stimulations.

The degree of synchronization S of the simulated neuronal population having a pathologically synchronous and oscillatory neuronal activity before, during and after a CR stimulation is shown in FIGS. 7A and 7B. The horizontal bars drawn at the top in the two illustrations indicate the time period in which the CR stimulation is applied. In the simulation shown in FIG. 7A, the sequences were varied at the start of each cycle, while the sequences in the simulation shown in FIG. 7B were only varied after a respective 100 cycles. The degree of synchronization S was calculated after every millisecond. The respective 50th percentile of the values for the degree of synchronization S is shown for three different stimulation strengths K in FIGS. 7A and 7B.

It can be seen as the result from FIGS. 7A and 7B that, with the exception of the CR stimulation with a stimulation strength K of 0.10, the slowly varying CR stimulation shown in FIG. 7B shows a larger and also longer-lasting stimulation success.

Figure 8A:
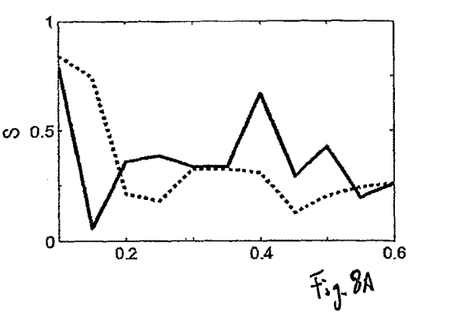

In addition to the stimulation strength K, the order of the sequences and the initial conditions of the network also have an influence on the stimulation success. This is shown in FIGS. 8A to 8D in which the degree of synchronization S is entered against the stimulation strength K. The simulations shown in FIGS. 8A and 8C are based on a variation of the sequences in each cycle, whereas the sequences were only varied after 100 cycles in the simulations shown in FIGS. 8B and 8D.

Figure 8B:
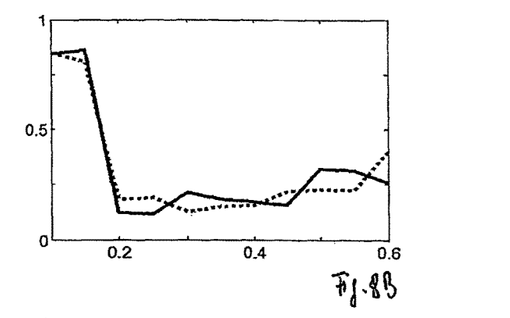
Figure 8C:
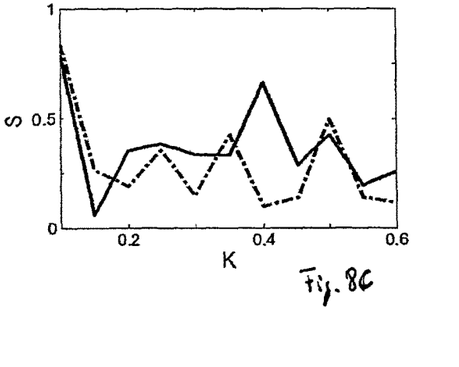

The respective 50th percentile of the values for the degree of synchronization S for the last 16 seconds of the simulation is shown in FIGS. 8A and 8B as a function of the stimulation strength K for two different orders of the sequences. The solid lines show the simulation results for the same order of the sequences such as also formed the basis for the simulations of FIGS. 7A and 7B, while the dotted lines represent the simulation results for another order. FIGS. 8A and 8B show that the slowly varying CR stimulation is more robust with respect to the order of the sequences in comparison with the fast-varying CR stimulation.

Figure 8D:
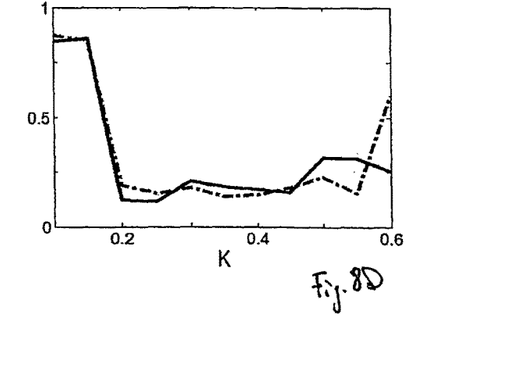

The simulations furthermore show that the initial conditions of the network also have an influence on the desynchronization of the neuronal activity. The respective 50th percentile of the values for the degree of synchronization S for the last 16 seconds of the stimulation are shown in FIGS. 8C and 8D as a function of the stimulation strength K for two different starting conditions of the sequences. The solid lines show the simulation results for the same starting conditions of the network such that also formed the basis of the simulations of FIGS. 7A and 7B, while the chain-dotted lines show the simulation results for different starting conditions. The slowly varying CR stimulation also proves to be more robust with respect to the starting conditions of the network in comparison with the fast-varying CR stimulation.

Figure 9A:
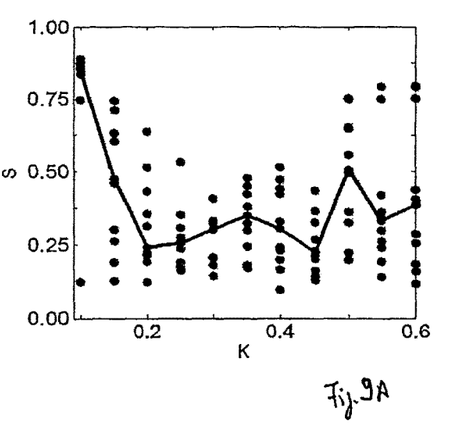
Figure 9B:
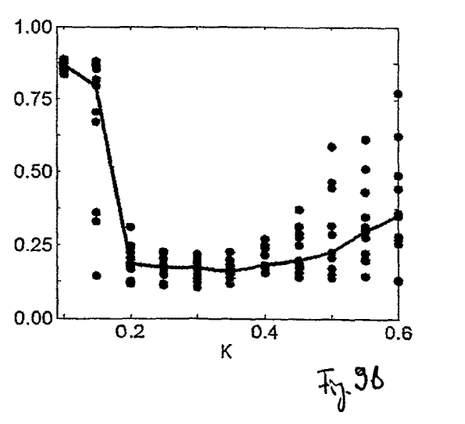

10 further simulations were carried out with different orders of the sequences and with different starting conditions of the network both for the fast-varying CR stimulation and for the slowly varying CR stimulation. The results of these simulations are shown in FIGS. 9A and 9B in which the 50th percentile of the values for the degree of synchronization S for the last 16 seconds of the stimulation is entered as a function of the stimulation strength K for different orders of the sequences and for different starting conditions of the network. The median of the results for each value of the stimulation strength K is connected by a line in each case. FIG. 9A shows the results of the fast-varying CR stimulation and FIG. 9B shows the results of the slowly varying CR stimulation. It can be seen as the result from FIGS. 9A and 9B that the slowly varying CR stimulation desynchronizes the highly synchronous network more and more robustly than is possible with the fast-varying CR stimulation.

The invention claimed is:

1. An apparatus for stimulating neurons, the apparatus comprising:
   a non-invasive stimulation unit configured to generate stimuli in a plurality of stimulation channels, wherein the stimuli is configured to stimulate a neuronal population in at least one of a brain and a spinal cord of a patient over the plurality of stimulation channels at respective different points; and a control unit configured to control the stimulation unit to generate sequences of the stimuli, such that an order of the plurality of stimulation channels in which the stimuli are generated within each sequence is kept constant for at least 20 sequences generated after one another and is varied after the at least 20 sequences, wherein the sequences are generated in a time pattern that comprises consecutive cycles, and wherein at least one respective sequence of stimuli is generated in at least a portion of the consecutive cycles, and wherein either exactly one sequence of stimuli is generated or no stimuli are generated within a respective cycle.

2. The apparatus in accordance with claim 1, wherein the stimuli comprise at least one of acoustic stimuli, visual stimuli, tactile stimuli, vibratory stimuli, thermal stimuli, olfactory stimuli, gustatory stimuli, transcutaneous electrical stimuli, transcutaneous magnetic stimuli, transcranial electrical stimuli, transcranial magnetic stimuli, and ultrasound stimuli.

3. The apparatus in accordance with claim 1, wherein the stimulation unit is configured to generate the stimuli in a respective stimulation channel to stimulate a respective subpopulation of the neuronal population and reset a phase of the neuronal activity of this subpopulation.

4. The apparatus in accordance with claim 1, wherein the stimulation unit generates exactly one stimulus within a respective sequence in each stimulation channel.

5. The apparatus in accordance with claim 4, wherein the exactly one stimulus is exactly one pulse train.

6. An apparatus for stimulating neurons, the apparatus comprising:
   a non-invasive stimulation unit configured to generate stimuli in a plurality of stimulation channels, wherein the stimuli is configured to stimulate a neuronal population in at least one of a brain and a spinal cord of a patient over the plurality of stimulation channels at respective different points; and
   a control unit configured to control the stimulation unit to generate sequences of the stimuli, such that an order of the plurality of stimulation channels in which the stimuli are generated within each sequence is kept constant for at least 20 sequences generated after one another and is varied after the at least 20 sequences,
   wherein the sequences are generated in a time pattern that comprises consecutive cycles, and wherein at least one respective sequence of stimuli is generated in at least a portion of the consecutive cycles,
   wherein stimuli are generated during n consecutive cycles and no stimuli are generated during m cycles following the n consecutive cycles, and
   wherein a pattern of the n consecutive cycles and following m cycles is periodically continued, wherein n and m are non-negative whole numbers.

7. The apparatus in accordance with claim 6, wherein the stimuli comprise at least one of acoustic stimuli, visual stimuli, tactile stimuli, vibratory stimuli, thermal stimuli, olfactory stimuli, gustatory stimuli, transcutaneous electrical stimuli, transcutaneous magnetic stimuli, transcranial electrical stimuli, transcranial magnetic stimuli, and ultrasound stimuli.

8. The apparatus in accordance with claim 6, wherein the stimulation unit is configured to generate the stimuli in a respective stimulation channel to stimulate a respective subpopulation of the neuronal population and reset a phase of the neuronal activity of this subpopulation.

9. An apparatus for stimulating neurons, the apparatus comprising:
   a non-invasive stimulation unit configured to generate stimuli in a plurality of stimulation channels, wherein the stimuli is configured to stimulate a neuronal population in at least one of a brain and a spinal cord of a patient over the plurality of stimulation channels at respective different points; and
   a control unit configured to control the stimulation unit to generate sequences of the stimuli, such that an order of the plurality of stimulation channels in which the stimuli are generated within each sequence is kept constant for at least 20 sequences generated after one another and is varied after the at least 20 sequences,
   wherein a pattern according to which the order of the plurality of stimulation channels in which the stimuli are generated within a sequence is kept constant for at least 20 sequences generated after one another and is varied after the at least 20 sequences is repeated a plurality of times.

10. The apparatus in accordance with claim 9, wherein the stimuli comprise at least one of acoustic stimuli, visual stimuli, tactile stimuli, vibratory stimuli, thermal stimuli, olfactory stimuli, gustatory stimuli, transcutaneous electrical stimuli, transcutaneous magnetic stimuli, transcranial electrical stimuli, transcranial magnetic stimuli, and ultrasound stimuli.

11. The apparatus in accordance with claim 9, wherein the stimulation unit is configured to generate the stimuli in a respective stimulation channel to stimulate a respective subpopulation of the neuronal population and reset a phase of the neuronal activity of this subpopulation.

12. An apparatus for stimulating neurons, the apparatus comprising:
   a non-invasive stimulation unit configured to generate stimuli in a plurality of stimulation channels, wherein the stimuli is configured to stimulate a neuronal population in at least one of a brain and a spinal cord of a patient over the plurality of stimulation channels at respective different points; and
   a control unit configured to control the stimulation unit to generate sequences of the stimuli, such that an order of the plurality of stimulation channels in which the stimuli are generated within each sequence is kept constant for at least 20 sequences generated after one another and is varied after the at least 20 sequences,
   wherein the stimuli are configured to suppress a pathologically synchronous and oscillatory activity of the neuron population on an administration to the patient over the plurality of stimulation channels, and
   wherein a duration of a cycle of the administration to the patient substantially corresponds to the mean period of the pathological oscillation of the neurons.

13. The apparatus in accordance with claim 12, wherein the stimuli comprise at least one of acoustic stimuli, visual stimuli, tactile stimuli, vibratory stimuli, thermal stimuli, olfactory stimuli, gustatory stimuli, transcutaneous electrical stimuli, transcutaneous magnetic stimuli, transcranial electrical stimuli, transcranial magnetic stimuli, and ultrasound stimuli.

14. The apparatus in accordance with claim 12, wherein the stimulation unit is configured to generate the stimuli in a respective stimulation channel to stimulate a respective subpopulation of the neuronal population and reset a phase of the neuronal activity of this subpopulation.

15. An apparatus for stimulating neurons, the apparatus comprising:

a non-invasive stimulation unit configured to generate stimuli in a plurality of stimulation channels, wherein the stimuli is configured to stimulate a neuronal population in at least one of a brain and a spinal cord of a patient over the plurality of stimulation channels at respective different points;

a control unit configured to control the stimulation unit to generate sequences of the stimuli, such that an order of the plurality of stimulation channels in which the stimuli are generated within each sequence is kept constant for at least 20 sequences generated after one another and is varied after the at least 20 sequences; and a measuring unit configured to record measured signals that reproduce a neuronal activity of the neuronal population stimulated by the stimuli, wherein the control unit is further configured to extend a number of the consecutively generated sequences in which the order of the plurality of stimulation channels in which the stimuli are generated within a sequence is constant when the control unit determines based on the measured signals that a degree of synchronization of the stimulated neuron population is not reduced by at least one predefined threshold value by application of the stimuli.

16. The apparatus in accordance with claim 15, wherein the stimuli comprise at least one of acoustic stimuli, visual stimuli, tactile stimuli, vibratory stimuli, thermal stimuli, olfactory stimuli, gustatory stimuli, transcutaneous electrical stimuli, transcutaneous magnetic stimuli, transcranial electrical stimuli, transcranial magnetic stimuli, and ultrasound stimuli.

17. The apparatus in accordance with claim 15, wherein the stimulation unit is configured to generate the stimuli in a respective stimulation channel to stimulate a respective subpopulation of the neuronal population and reset a phase of the neuronal activity of this subpopulation.

18. A method of stimulating neurons comprising:

generating, by a non-invasive stimulation unit, stimuli in a plurality of stimulation channels, wherein the stimuli stimulate a neuronal population in at least one of brain and a spinal cord of a patient over the plurality of stimulation channels at respective different points;

repetitively generating, by the non-invasive stimulation unit, sequences of the stimuli;

maintaining an order of the plurality of stimulation channels in which the stimuli are generated within in sequence as constant for at least 20 sequences generated after one another;

varying the order after the at least 20 sequences;

recording measured signals that reproduce a neuronal activity of the neuronal population stimulated by the stimuli; and extending a number of the consecutively generated sequences in which the order of the plurality of stimulation channels in which the stimuli are generated within sequence is constant when, based on the measured signals, a degree of synchronization of the stimulated neuron population is not reduced by at least one predefined threshold value by application of the stimuli.

19. A computer program product for execution in a data processing system, the computer program product including instructions for:

generating, by a non-invasive stimulation unit, stimuli in a plurality of stimulation channels, wherein the stimuli stimulate a neuronal population in at least one of brain and a spinal cord of a patient over the plurality of stimulation channels at respective different points;

repetitively generating, by the non-invasive stimulation unit, sequences of the stimuli;

maintaining an order of the plurality of stimulation channels in which the stimuli are generated within in sequence as constant for at least 20 sequences generated after one another;

varying the order after the at least 20 sequences;

recording measured signals that reproduce a neuronal activity of the neuronal population stimulated by the stimuli; and extending a number of the consecutively generated sequences in which the order of the plurality of stimulation channels in which the stimuli are generated within sequence is constant when, based on the measured signals, a degree of synchronization of the stimulated neuron population is not reduced by at least one predefined threshold value by application of the stimuli.

* * * * *